United States Patent [19]

Notton

[11] 4,263,681
[45] Apr. 28, 1981

[54] COATED METALLIC BONE JOINT PROSTHESIS RESISTANT TO SYNOVIAL FLUID CORROSION

[75] Inventor: John H. F. Notton, Reading, England

[73] Assignee: Johnson, Matthey & Co., Limited, London, England

[21] Appl. No.: 911,192

[22] Filed: May 30, 1978

[30] Foreign Application Priority Data

Jun. 2, 1977 [GB] United Kingdom ............... 23448/77

[51] Int. Cl.³ .............................................. A61F 1/00
[52] U.S. Cl. ....................................... 3/1.91; 3/1.912; 128/92 C; 128/92 D; 204/23; 204/39
[58] Field of Search ................................ 3/1.9–1.913, 3/1; 128/92 C, 92 CA, 92 R, 92 B, 92 D; 32/10 A; 433/201

[56] References Cited

U.S. PATENT DOCUMENTS

| | | | |
|---|---|---|---|
| 3,605,123 | 9/1971 | Hahn | 3/1.9 |
| 3,826,241 | 7/1974 | Bucalo | 32/10 A X |
| 4,145,764 | 3/1979 | Suzuki et al. | 3/1.9 |

FOREIGN PATENT DOCUMENTS

| | | | |
|---|---|---|---|
| 2184159 | 12/1973 | France | 3/1.912 |
| 170872 | 10/1934 | Switzerland | 32/10 A |

*Primary Examiner*—Ronald L. Frinks
*Attorney, Agent, or Firm*—Cushman, Darby & Cushman

[57] ABSTRACT

A metallic bone joint prosthesis having articulating surfaces which include an outer layer or coating comprising platinum, ruthenium, iridium or alloy thereof.

4 Claims, No Drawings

COATED METALLIC BONE JOINT PROSTHESIS RESISTANT TO SYNOVIAL FLUID CORROSION

This invention relates to prosthesis. More particularly, the invention relates to bone prosthesis, such prosthetic devices being in the form of both joints and repair plates.

Throughout the remainder of this specification, it is to be understood that the word "prosthesis" refers either to an entire prosthetic device or to one or more individual components of such a device, as appropriate.

It is now established practice in bone prosthetic surgery to utilise metallic components for at least part of a bone prosthesis. Such prostheses commonly fall within one of two general types, namely joints and repair plates. Replacement joints and repair plates are required to perform radically different functions, and it is therefore convenient to consider each type separately.

A suitable example of a bone joint prosthesis is a hip joint which is dynamically the most simple of the main limb joints. The nature of such a prosthesis is determined according to the needs of the individual patient. Most repairs are carried out on older persons who typically fracture the neck of the femur. Since life expectancy of the patient is usually limited, say to about five years, and activity loading is low, the relatively simple technique of fitting a new neck and ball prosthesis to the femur to engage in the natural hip socket is often used. Stainless steel is commonly utilized as the material of the prosthesis despite the occasional occurrence of tissue/corrosion reactions.

For a younger patient having a longer life expectancy, and in cases where the joint is diseased, the entire joint is replaced. Generally a metallic ball on the femur engages a plastics socket which is rigidly fixed to the hip bone. The plastics material used is generally high density polythene and the metallic material is generally either a "Stellite" (Registered Trade Mark) alloy or stainless steel. Typically, a relatively large amount of wear occurs on the plastics material but very little on the metal and wear debris so produced may prove to be toxic.

The loading on an articulating surface varies according to the particular joint under consideration but for a hip joint a loading of 100–300 lb./in$^2$ is common. Additionally, a hip joint may be expected to execute as many as $2 \times 10^6$ movements per year, which movements include impact loading as well as simple articulation. Lubrication is thus essential but the natural joint lubrication medium, known as synovial fluid, is acidic and tends to corrode metal surfaces. It is for this reason that metal-to-metal prostheses have not hitherto been particularly successful.

Repair plate prostheses, on the other hand, do not have to be capable of undergoing movement, being used merely to join the broken ends of a bone arising from a simple fracture, especially where correct realignment of the bone cannot be achieved by external means. Their function is therefore essentially temporary in that once the bone has mended the plates are no longer required. They are, however, left in place. They therefore need to be of sufficient strength to provide the necessary support and they must also be capable of withstanding prolonged periods, usually many years, of contact with body fluids. In recent years, titanium has been the preferred material for repair plates.

It is therefore one object of the present invention to provide a metallic bone joint prosthesis that is resistant to corrosion.

It is a further object of the invention to provide a metallic bone joint prosthesis, the articulating surface of which has superior tribological properties to metallic prostheses in current usage.

It is yet a further object of the invention to provide a metallic bone joint prosthesis the wear debris of which is relatively non-toxic.

According to the invention, we provide a metallic bone prosthesis having on at least part of its surface a layer or a deposit comprising platinum, ruthenium or iridium or an alloy containing at least one of said metals, and optionally palladium, rhodium, gold and/or a base metal. Suitable base metals and alloying constituents include copper, iron, nickel, cobalt, tungsten and molybdenum. Preferably, the alloy or alloying constituent is chosen having regard to the fact that the layer of metal or alloy will tend to work-harden during use.

In the case of a metallic bone joint prosthesis according to the invention, at least the articulating surface is coated with a layer of platinum, ruthenium or iridium or an alloy containing at least one of said metals. Since the said layer is resistant to corrosion by synovial fluid, we are able to provide an improved bone joint prosthesis wherein at least two, or all, mutually articulated components are metallic, at least the articulating surface thereof being coated with the said layer.

For reasons that are explained hereinafter, it is preferred that substantially the entire surface of a metallic prosthesis is coated according to the invention with a layer of platinum, ruthenium or iridium or an alloy containing at least one of said metals.

The layer of platinum, ruthenium or iridium metal or alloy typically has a thickness up to about 10 thou inch. For a bone joint prosthesis wherein at least two, or all, mutually articulated components are metallic, although it is within the scope of the invention and adequate in order to achieve the desired tribological properties to coat only one of any two mutually articulating surfaces, we prefer that both such surfaces are coated to avoid the possibility of setting up an electrical cell between dissimilar metallic materials utilising body fluids as electrolyte. In such a case, selecting the hip joint as an example, the layer on the ball wound typically be about 10 thou in thickness while the layer on the socket would typically be about 1 thou in thickness, although other thicknesses are possible. However, the thickness of the layers on both the ball and the socket (or any other co-operating surfaces of a prosthesis) may have a thickness falling within the range 5 to 50 thou inch, depending on the type of joint. In use, however, one or both layers applied to co-operating components will naturally become thinner.

The metallic material from which the prosthesis is made and which is coated according to the invention may be any suitable metal or alloy. We have found that, for joint prosthesis, stainless steel or a "Stellite" alloy, such as are currently used in metallic/plastics joints, are satisfactory. Another suitable material which may be used, either in joint or repair plate prostheses according to the invention, is titanium. This material, having high strength, is currently in use for the manufacture of repair plate prostheses but has not hitherto been used for bone joint prostheses since the hard oxide surface layer is very abrasive. A layer of platinum, ruthenium or iridium, according to the invention, on at least the articulating surface or surfaces of a titanium bone joint prosthesis overcomes this problem. If a prosthesis, either as a bone joint or repair plate, is entirely coated with a layer of platinum, ruthenium or iridium metal or alloy, then the metallic material from which the prosthesis is made may be selected solely according to the physical properties, for example strength, workability and so on, with no account being taken of properties such as compatability in vivo. For example, a high carbon steel would provide the necessary strength and would have the additional advantage of being relatively cheap. These considerations are especially true of repair plate prostheses, the surfaces of which, not being articulating, are not subject to abrasion or other action which could cause the surface layer or coating to lose its integrity, thus exposing to body fluids and tissue the metallic material of the prosthesis.

The hardness of the layer of platinum, ruthenium or iridium metal or alloy is of critical importance. For a repair plate prosthesis, where corrosion resistance is the prime consideration, a hardness in excess of 400 Hv is desirable. On the other hand, for a bone joint prosthesis, a rather lower hardness, say 50 Hv for example, results in better bearing properties. For all applications the coating should be adherent and substantially pore free.

The layer of platinum, ruthenium or iridium metal or alloy according to the invention may be applied by any of the techniques known in the art provided that the resulting layer has the desired physical properties. Examples of techniques which may be considered are the fused salt process and aqueous electroplating processes. Optionally, the coating can be annealed.

The fused salt process typically uses, as electrolyte, a eutectic salt mixture containing 53% sodium cyanide and 47% potassium cyanide, the melting temperature being about 520° C. The prostheses to be plated are immersed, suitably masked if only part of the surface is to be plated, in the molten electrolyte as cathodes; the anodes may be either of consumable sheet platinum or alloy which it is desired to apply to the prostheses or of insoluble material, the platinum and any other metals being added to the electrolyte as salts which, of course, need to be replenished from time to time. Control of the plating thickness is achieved by varying either the plating current or the electroplating time, or both.

Hardness values and wear resistance of "Stellite" and platinum are given in the following Table. The figures for wear resistance relate to the volume loss in cubic centimeters per centimeters sliding distance from the tip of a pin of the test material impinging on a rotating disc of Stellite.

| | Hardness $H_v$ | Wear Resistance | |
|---|---|---|---|
| | | No lubrication | Lubricated with distilled water |
| Stellite | 350–400 | $4.5 \times 10^{-9}$ | $0.8 \times 10^{-9}$ |
| Platinum | | | |
| annealed (solid pin) | 50 | $6 \times 10^{-9}$ | $0.1 \times 10^{-9}$ |
| plated on Stellite | 70 | $0.7 \times 10^{-9}$ | $0.05 \times 10^{-9}$ |
| as drawn (solid pin) | 110 | $3 \times 10^{-9}$ | $0.7 \times 10^{-9}$ |

Additionally, the following Table illustrates the range of hardness obtained by utilizing alloys rather than pure platinum. The results relate to fully annealed coatings but the figures can be expected to be of the same order of magnitude as for fused salt-applied coatings since the high operating temperatures of the fused salt bath results in a coating which can be considered to be annealed as plated.

| | | |
|---|---|---|
| 4.5% Cu/Pt | 110 Hv | |
| 4.5% Ru/Pt | 120 Hv | |
| 4.5 | Pd/Pt | 70 Hv |
| 4.5% Ir/Pt | 70 Hv | |
| 4.5% Co/Pt | 130 Hv | |
| 2% Ni/2.5% Pd/Pt | 104 Hv | |
| 1% Rh/3.5% Au/Pt | 90 Hv | |
| 1% Ir/3.5% Pd/Pt | 60 Hv | |
| 5% Mo/Pt | 170 Hv | |

A further advantage of the invention, with respect to bone joint prostheses, is that the articulating surfaces do not necessarily need to be polished. Using standard metallic prostheses, it is recommended that the surface finish should be less than 0.025 microns c.l.a. and the departure from roundness should be less than 5 microns m.v.s. According to the invention, a relatively soft layer of platinum, for example, say 10 to 15 thou inch in thickness, coated on the ball of a ball and socket joint, will, when the articulating surfaces are brought into contact and moved relatively to one another under pressure, transfer a thin layer of platinum onto the articulating surface of the socket so that the articulating surfaces bed in and substantially perfectly adapt to each other.

We have found that platinum is the preferred coating material for metal-to-metal prostheses whereas ruthenium and iridium are more suitable for coating at least the metallic articulating surface of a metal-to-plastics prosthesis. Alloying ingredients may be introduced, say, to harden the coating layer but, as mentioned previously, due regard should be paid to the possibility of work hardening during use.

Bone joint prostheses according to the invention may be used in either the lubricated or unlubricated condition. By "unlubricated" we mean, of course, devoid of artificially introduced lubricant.

Clearly, although bone joint prostheses have been discussed mainly with reference to the hip joint, the invention is equally applicable to prostheses having a more complex dynamic function, for example as total or partial replacements for the knee or elbow.

What we claim is:

1. A metal-to-metal bone joint prosthesis which is resistant to corrosion caused by synovial fluids comprising at least two articulated metal members each having an articulating surface which would normally be subject to corrosion caused by synovial fluids, each of said articulating surfaces being coated over its entire area with an adherent and substantially pore free layer comprising at least one member of the group consisting of platinum, ruthenium, iridium and alloys containing at least one of said metals and at least one member of the group consisting of palladium, rhodium, gold and a base metal, each of said layers being resistant to corrosion by sinovial fluid to thereby protect said metal members against corrosion.

2. A prosthesis according to claim 1 wherein the alloy includes a base metal selected from the group consisting of copper, iron, nickel, cobalt, tungsten and molybdenum.

3. A prosthesis according to claim 1 wherein the layers are applied to a substrate selected from the group consisting of stainless steel and titanium substrates.

4. A prosthesis according to claim 1 wherein the said layers have a thickness within the range 5 to 50 thousands of an inch.

* * * * *